United States Patent

Smith et al.

[11] Patent Number: 5,858,905
[45] Date of Patent: Jan. 12, 1999

[54] PYROPHOSPHITE LIGANDS AND THEIR USE IN TRANSITION METAL CATALYZED PROCESSES

[75] Inventors: Andrea R. Smith, Wingdale, N.Y.; Stephen D. Pastor, Danbury, Conn.

[73] Assignee: Ciba Specialty Chemicals Corporation, Tarrytown, N.Y.

[21] Appl. No.: 898,827

[22] Filed: Jul. 23, 1997

[51] Int. Cl.⁶ .............. B01J 31/00; C07F 13/00; C07F 15/00; C07F 7/22
[52] U.S. Cl. .............. 502/162; 502/165; 502/166; 502/168; 556/17; 556/45; 556/110; 556/136; 556/138
[58] Field of Search .............. 502/162, 165, 502/166; 556/17

[56] References Cited

U.S. PATENT DOCUMENTS

| | | | |
|---|---|---|---|
| 2,722,539 | 11/1955 | Anderson | 260/461 |
| 3,475,509 | 10/1969 | Hata et al. | 502/162 |
| 5,475,042 | 12/1995 | Shum et al. | 524/119 |
| 5,631,345 | 5/1997 | Takaya et al. | 502/162 |
| 5,654,455 | 8/1997 | Pastor et al. | 556/13 |
| 5,817,850 | 10/1998 | Pastor et al. | 502/162 |

OTHER PUBLICATIONS

R. Carreño et al., Organometallics, 1994, 13, pp. 993–1004.
M. A. Alnarez et al., Organomettalics, 1997, 16, pp. 2581–2589.
P.C. Crofts, et al. J. Chem. Soc. 1958, 4250–4254.
G. W. Anderson, et al., J. Am. Chem., Soc, 1952, 74, pp. 5309–5312.
I.F. Lutsenko, et al, Pure & Appl. Chem. 52, pp. 917–944 (1980).

*Primary Examiner*—Mark L. Bell
*Assistant Examiner*—J. Pasterczyk
*Attorney, Agent, or Firm*—Luther A. R. Hall; Jacob M. Levine

[57] ABSTRACT

Catalyst systems which comprise a transition metal and a pyrophosphite ligand are particularly effective as catalysts for hydrosilation reactions. The transition metal is from groups 7–11 of the Periodic Table, and the pyrophosphite has the following formula:

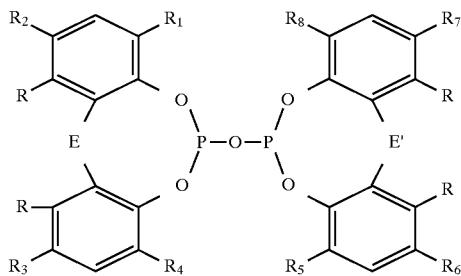

wherein E and E' are independently a direct bond, —S—, —Se—, or —$CR_9R_{10}$— where $R_9$ and $R_{10}$ are independently hydrogen or alkyl of 1–18 carbon atoms, and $R_{10}$ can also be phenyl. R is H or methyl, $R_{1-8}$ are independently H, $C_{1-18}$ alkyl, $C_{5-12}$ cycloalkyl, or $C_{7-15}$ phenylalkyl.

7 Claims, No Drawings

PYROPHOSPHITE LIGANDS AND THEIR USE IN TRANSITION METAL CATALYZED PROCESSES

The instant invention pertains to novel catalysts which comprise a transition metal and a hindered pyrophosphite ligand which are useful in transition metal catalyzed processes, particularly hydrosilation reactions.

BACKGROUND OF THE INVENTION

The hindered pyrophosphites of this invention are disclosed in U.S. Pat. No. 5,475,042 as useful stabilizers for a host of organic substrates.

The general description of hydrosilation processes is given in copending and allowed U.S. patent application Ser. No. 08/576,629, now U.S. Pat. No. 5,659,455.

The use of tetraethyl pyrophosphites as a ligand is reported by R. Carreño et al., Organometallics, 1994, 13, 993 and by M. A. Alvarez et al., Organometallics, 1997, 16, 2581 where only the X-ray structure and NMR spectra of the complexes are given. A bis-o-phenylene pyrophosphite is described as a reagent for peptide synthesis by P. C. Crofts et al., J. Chem. Soc., 1958, 4250. Similarly, the use of tetraethyl pyrophosphite is also described as a reagent for peptide synthesis by G. W. Anderson et al., J. Am. Chem. Soc, 1952, 74, 5309 and disclosed in U.S. Pat. No. 2,722, 539. The use of the instant hindered pyrophosphites in transition-metal-catalyzed reactions has not been reported.

OBJECT OF THE INVENTION

The use of sterically hindered pyrophosphites as ligands for the transition-metal-catalyzed reactions.

DETAILED DESCRIPTION

The instant invention pertains to a transition metal ligand complex catalyst system which comprises (a) a transition metal selected from Groups 7–11 of the periodic table; and (b) a sterically hindered pyrophosphite of formula I

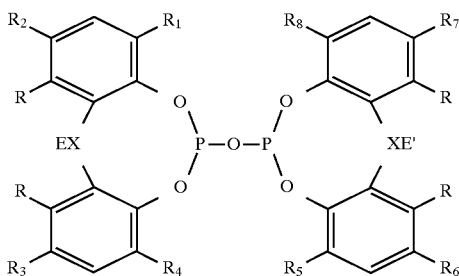

wherein
R is independently hydrogen or methyl,
$R_1$, $R_2$, $R_3$, $R_4$, $R_5$, $R_6$, $R_7$ and $R_8$ are independently hydrogen, alkyl of 1 to 18 carbon atoms, cycloalkyl of 5 to 12 carbon atoms or phenylalkyl of 7 to 15 carbon atoms, and
E and E' are independently a direct bond, —S—, —Se— or —$CR_9R_{10}$— where $R_9$ and $R_{10}$ are independently hydrogen or alkyl of 1 to 18 carbon atoms, or $R_{10}$ is also phenyl.

The transition metal is preferably selected from groups 8–11 of the periodic table; most preferably groups 8–10; especially rhodium or platinum; particularly rhodium.

Preferably, R is hydrogen; $R_1$, $R_4$, $R_5$ and $R_8$ are tert-butyl; and $R_2$, $R_3$, $R_6$ and $R_7$ are hydrogen, methyl or tert-butyl.

Preferably, E and E' are each a direct bond, methylene or ethylidene.

The instant invention is also to a process for the hydrosilation of ketones, aldehydes or other compounds containing an ethylenically unsaturated double bond which comprises reacting the ketone, aldehyde or unsaturated compound with a silane compound in the presence of a transition metal ligand complex catalyst system as described above.

The advantages of the instant invention lies in the fact that the ligands of invention are hydrolytically stable and easy to handle; and that they are stable to reaction conditions that would decompose other pyrophosphites such as tetraethyl pyrophosphite. The reaction of simple pyrophosphites in peptide synthesis is illustrative of this. Furthermore, the instant ligands do not show diphosphine oxide⇌pyrophosphite tautomerism, which allows the synthesis of defined structures. See the review article by I. F. Lutsenko et al., Pure & Appl. Chem. 52, 917.

When any of $R_1$ to $R_{10}$, is alkyl, such alkyl groups are, for example, methyl, ethyl, isopropyl, n-butyl, tert-butyl, tert-amyl, 2-ethylhexyl, n-octyl, n-undecyl, lauryl, n-heptadecyl and n-octadecyl; when cycloalkyl, they are, for example, cyclopentyl, cyclohexyl, 1-methylcyclohexyl, cyclooctyl and cyclododecyl; or when phenylalkyl, they are, for example, benzyl, 1-phenylethyl, 2-phenylethyl and αα-dimethylbenzyl; so that —$CR_9R_{10}$ is, for example, methylene, ethylidene, 2,2-isopropylidene, 1,1- butylidene, 1,1-octylidene and benzylidene.

The following examples are for illustrative purposes only and are not to be construed to limit the scope of the instant invention in any manner whatsoever.

EXAMPLE 1

6-Chloro-2,4,8,10-tetra-tert-butyl-dibenzo[d,f][1,3,2] dioxaphosphepin

To a solution of 55.2 g (130 mmol) of 2,2'-bis(4,6-di-tert-butylphenol) and 1.82 mL (19 mmol) of 1-methyl-2-pyrrolidinone in 400 mL of toluene at ambient temperature is added dropwise 16.6 mL (19 mmol) of phosphorus trichloride. After the addition is complete, the reaction mixture is heated at reflux for 18 hours. After cooling to ambient temperature, the toluene is removed in vacuo from the reaction mass. The reaction mass is then recrystallized from 300 mL of acetonitrile. The recrystallization solvent is decanted from the reaction residue whichis then dried under vacuum to give 39.9 g (64.5%) yield of an off-white solid as the title compound melting at 183°–186° C.
Analysis:
  Calcd for $C_{28}H_{40}ClO_2P$: C, 70.8; H, 8.4.
  Found: C,70.6; H,8.5.

EXAMPLE 2

6-Oxo-2,4,8,10-tetra-tert-butyl-dibenzo[d,f][1,3,2] dioxaphosphepin

To a solution of 6.32 g (13 mmol) of the compound of Example 1 in 150 mL of toluene at ambient temperature is added dropwise a solution of 0.24 mL (13 mmol) of distilled water in 3.0 mL (22 mmol) of triethylamine. After the addition is complete, the reaction mixture is stirred at ambient temperature for 15 minutes. The reaction solvent is removed in vacue and the reaction mass is then recrystallized twice with 50 mL of acetonitrile. The recrystallization solvent is removed under vacuum and the residue is dried under vacuum to afford the title compound in a yield of 5.2 g (86.3%) as an off-white solid melting at 218° C.
Analysis:
Calcd for $C_{28}H_{41}O_3P$: C, 73.6; H, 9.1.
Found: C, 73.2; H, 9.7.

EXAMPLE 3

6-{[2,4,8,10-Tetra-tert-butyl-dibenzo[d,f][1,3,2]dioxaphosphepin-6-yl]oxy}-2,4,8,10-tetra-tert-butyl-dibenzo[d,f][1,3,2]dioxaphosphepin To a suspension of 0.18 g (7.5 mmol) of sodium hydride in 50 mL of dry tetrahydrofuran is added dropwise a solution of 3.56 g (7.8 mmol) of the compound of Example 2 in 80 mL of dry tetrahydrofuran. After addition is complete, the reaction mixture is heated to 60° C. for 9.5 hours. The reaction mixture is then cooled to about 0° C. To the reaction mixture is added 3.67 g (7.7 mmol) of the compound of Example 1 at 3° C. The reaction mixture is stirred for 14 hours at ambient temperature. The reaction solvent is removed under vacuum and the residue is a crude product which is purified by chromatography (hexane:ethyl acetate; 95:5). The purified product is then recrystallized once from acetonitrile and then from 2-butanone to yield the title compound as a white solid melting at 269° C.
Analysis:
Calcd for $C_{56}H_{80}O_5P_2$: C, 75.1; H, 9.0.
Found: C, 74.8; H, 9.1.

EXAMPLE 4

6-Chloro-2,4,8,10-tetra-tert-butyl- 12H-dibenzo[d,g][1,3,2]dioxaphosphocin

To a solution of 25.0 g (0.059 mol) of 2,2'-methylenebis (4,6-di-tert-butylphenol) and 0.57 mL (5.9 mmol) of 1-methyl-2-pyrrolidinone in 275 mL of toluene at ambient temperature is added dropwise 5.16 mL (0.059 mol) of phosphorus trichloride. After the addition is complete, the reaction mixture is refluxed for eight hours. After cooling the mixture to ambient temperature, the toluene is removed in vacuo and the reaction mass is recrystallized twice from 250 mL of 98% acetonitrile and 2% toluene (% by volume) in acetonitrile. The recrystallization solvent is removed by decantation and the residue is dried under vacuum to give 21.4 g (79% yield) of the title compound as an off-white solid melting at 227°–230° C.
Analysis:
Calcd for $C_{29}H_{42}ClO_2P$: C, 71.2; H, 8.7.
Found: C, 71.1; H, 8.9.

EXAMPLE 5

6-Oxo-2,4,8,10-tetra-tert-butyl-12H-dibenzo[d,g][1,3,2]dioxaphosphocin

To a solution of 8.9 g (0.019 mol) of the compound of Example 4 in 150 mL of toluene at ambient temperature is added dropwise a solution of 0.34 mL (0.019 mol) of distilled water in 4.0 mL (0.029 mol) of triethylamine. After the addition is complete, the reaction mixture is stirred at ambient temperature for 15 minutes. The reaction solvent is removed under vacuum and the residue is recrystallized twice with 50 mL of acetonitrile. The acetonitrile is then removed in vacuo and the residue is dried under vacuum to give 2.4 g (79.5% yield) of the title compound as an off-white solid melting at 164° C.
Analysis:
Calcd for $C_{29}H_{43}O_3P$: C, 74.0; H, 9.2.
Found: C, 73.3; H, 9.8.

EXAMPLE 6

6-{[2,4,8,10-Tetra-tert-butyl-12H-dibenzo[d,g][1,3,2]dioxaphosphocin-6-yl]oxy}-2,4,8,10-tetra-tert-butyl-12H-dibenzo[d,g][1,3,2]dioxaphosphocin To a solution of 2.0 g (4.3 mmol) of the compound of Example 5 in 150 mL of toluene is added 2.1 g (4.3 mmol) of the compound of Example 4 and 3.0 mL (22 mmol) of triethylamine at ambient temperature. The reaction mixture is stirred at room temperature for 14 hours. The solvent is removed under vacuum and the residue is recrystallized twice from acetonitrile to give the title compound as a white solid melting at 249°–252° C.
Analysis:
Calcd for $C_{58}H_{84}O_5P_2$: C, 75.4; H, 9.2.
Found: C, 75.1; H, 9.5.

EXAMPLE 7

6-Chloro-2,4,8,10-tetra-tert-butyl-12-methyl-dibenzo[d,g][1,3,2]dioxaphosphocin

To a solution of 50.9 g. (0.12 mol) of 2,2'-ethylidenebis (4,6-di-tert-butylphenol) and 1.73 mL (0.018 mol) of 1-methyl-2-pyrrolidinone in 275 mL of toluene at ambient temperature is added dropwise 15.7 mL (0.18 mol) of phosphorus trichloride. After the addition is complete, the reaction mixture is heated at reflux for 18 hours. After cooling to room temperature, the toluene is removed in vacuo and the residue is then recrystallized twice from 250 mL of acetonitrile. The acetonitrile is decanted from the product which is dried under vacuum to give 21.0 g (34.8% yield) of the title compound as an off-white solid melting at 194°–198° C.
Analysis:
Calcd for $C_{30}H44ClO_2P$: C, 71.6; H, 8.8.
Found: C, 71.6; H, 9.1.

EXAMPLE 8

6-Oxo-2,4,8,10-tetra-tert-butyl-12-methyl-dibenzo[d,g][1,3,2]dioxaphosphocin

To a solution of 5.5 g (11 mmol) of the compound of Example 7 in 100 mL of toluene at ambient temperature is added dropwise a solution of 0.20 mL (11 mmol) of distilled water in 3.0 mL (22 mmol) of triethylamine. After the addition is complete, the reaction mixture is stirred at room temperature for 15 minutes. The toluene is removed under vacuum and the residue is recrystallized twice from 50 mL of diethyl ether. The ether is removed in vacuo and the residue is dried under vacuum to give 3.95 g (74% yield) of the title compound as an off-white solid melting at 209° C.
Analysis:
Calcd for $C_{30}H_{45}O_3P$: C, 74.3; H, 9.4.
Found: C, 74.0; H, 9.9.

EXAMPLE 9

6-{[2,4,8,10-Tetra-tert-butyl-12-methyl-dibenzo[d,g][1,3,2]dioxaphosphocin-6-yl]oxy}-2,4,8,10-tetra-tert-butyl-12-methyl-dibenzo[d,g][1,3,2]dioxaphosphocin To a solution of 17.3 g (36 mmol) of the compound of Example 8 in 250 mL of dry tetrahydrofuran (THF) is added 1.0 g (41 mmol) of sodium hydride at 3° C. After the addition is complete, the reaction mixture is allowed to warm to room temperature. The reaction mixture is stirred for 14 hours at ambient temperature. To the reaction mixture is then added 14.8 g(29 mmol) of the compound of Example 7 at ambient temperature. After 48 hours, the reaction mixture is filtered and the filtrate is concentrated under vacuum. The residue is purified by flash chromatography with 1% ethyl acetate/99% hexane to give the tide compound as a white solid melting at 281°–285° C.
Analysis:

Calcd for $C_{60}H_{88}O_5P_2$: C, 75.7; H, 9.3.

Found: C, 75.3; H, 9.7.

EXAMPLE 10

This Example shows the complex formation of the compound of Example 3 with rhodium. To a solution of 0.0435 g (0.0486 mmol) of the pyrophosphite of Example 3 in 0.5 mL of deuterobenzene is added 0.006 g (0.0122 mmol) of chloro(1,5-cyclooctadiene)-rhodium(I) dimer. In the $^{31}P\{^1H\}$ NMR spectrum of the resultant reaction mixture, multiplets are observed at $\delta 127.1$ (d, J=45.3 Hz), $\delta 117.2$ (dd, $J_{pp}$=45.3 Hz, $J_{PRh}$=274.1 Hz) and $\delta 114.9$ (dd, $J_{pp}$=45.3 Hz, $J_{PRh}$=274.1 Hz) for the instant rhodium complex.

EXAMPLE 11

This Example illustrates the complex formation of the pyrophosphite of Example 6 with platinum. To a solution of 0.0286 g (0.031 mmol) of the pyrophosphite of Example 6 in 1 mL of deuterobenzene is added 0.0117 g (0.031 mmol) of (1,5-cyclooctadiene)-platinum (II) chloride. In the $^{31}P\{H\}$ NMR spectrum of the resultant reaction mixture, multiplets are observed at $\delta 114.0$ (dd, J=37 Hz, J=1119 Hz), $\delta 51.4$ (dd, J=42 Hz, J=1119Hz), and $\delta 52.2$ (J=38 Hz, J=42 Hz) for resultant platinum complex.

EXAMPLE 12

This Example shows the complex formation of the pyrophosphite of Example 6 with rhodium. To a solution of 0.0828 g (0.0896 mmol) of the pyrophosphite of Example 6 in 0.5 mL of deuterobenzene is added 0.0224 g (0.0455 mmol) of chloro(1,5-cyclooctadiene)rhodium(I) dimer. In the $^{31}P\{^1H\}$ NMR spectrum of the resultant reaction mixture, multiplets are observed at $\delta 79.5$ (dd, J=134 Hz, J=292 Hz) and $\delta 63.9$ (dd, J=134 Hz, J=303 Hz) for the resultant rhodium complex.

EXAMPLE 13

Transition-metal-catalyzed Hydrosilation of 2-Heptanone

To a stirred solution of 1.1 mL (5.93 mmol) of diphenylsilane and 0.72 mL (5.17 mmol) of 2-heptanone in 6 mL of benzene is added dropwise over 30 minutes a solution of preformed catalyst prepared from 0.0186 g (0.0377 mmol) of 1,5-cyclooctadiene rhodium(I) chloride dimer and 0.0743 g (0.0805 mmol) of the pyrophosphite of Example 6. The reaction mixture is stirred overnight and then to the reaction mixture is added 3.5 mL of methanol, 1.5 mL of water and 1 mL of 5N aqueous sodium hydroxide solution. The reaction mixture is stirred for 15 minutes and the organic layer is then separated. The aqueous layer is extracted three times with 5 mL of diethyl ether. The organic phases are combined and then dried over anhydrous sodium sulfate. The organic solvents are removed under vacuum. The $^1H$ NMR spectrum of the residue shows complete conversion to 2-heptanol and no evidence of starting ketone. The 2-heptanol is purified by filtration through silica gel to give 0.30 g (50% yield) of 2-heptanol.

EXAMPLE 14

Transition-metal-catalyzed Hydrosilation of 2-Heptanone

To a stirred solution of 1.1 mL (5.93 mmol) of diphenylsilane and 0.72 mL (5.17 mmol) of 2-heptanone in 6 mL of benzene is added dropwise over 30 minutes a solution of preformed catalyst prepared from 0.0187 g (0.0379 mmol) of 1,5-cyclooctadiene rhodium(I) chloride dimer and 0.0725 g (0.0762 mmol) of the pyrophosphite of Example 9. The reaction mixture is stirred overnight and then to the reaction mixture is added 3.5 mL of methanol, 1.5 mL of water and 1 mL of 5N aqueous sodium hydroxide solution. The reaction mixture is stirred for 15 minutes and the organic layer is then separated. The aqueous layer is extracted three times with 5 mL of diethyl ether. The organic phases are combined and then dried over anhydrous sodium sulfate. The organic solvents are removed under vacuum. The $^1H$ NMR spectrum of the residue shows complete conversion to 2-heptanol and no evidence of starting ketone. The 2-heptanol is purified by filtration through silica gel to give 0.38 g (63% yield) of 2-heptanol.

What is claimed is:

1. A transition metal ligand complex catalyst system which comprises
    (a) a transition metal selected from Groups 7–11 of the periodic table; and
    (b) a pyrophosphite of formula I

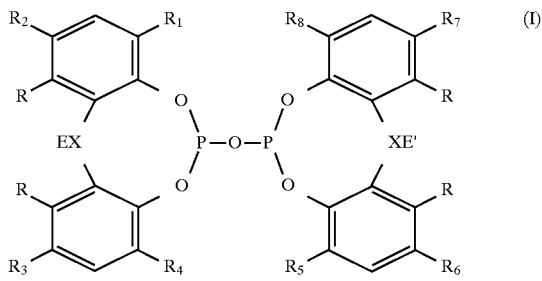

wherein

R is independently hydrogen or methyl, $R_1$, $R_2$, $R_3$, $R_4$, $R_5$, $R_6$, $R_7$ and $R_8$ are independently hydrogen, alkyl of 1 to 18 carbon atoms, cycloalkyl of 5 to 12 carbon atoms or phenylalkyl of 7 to 15 carbon atoms, and E and E' are independently a direct bond, —S—, —Se— or —$CR_9R_{10}$— where $R_9$ and $R_{10}$ are independently hydrogen or alkyl of 1 to 18 carbon atoms, or $R_{10}$ is also phenyl.

2. A catalyst system according to claim 1 wherein the transition metal is selected from groups 8–11 of the periodic table.

3. A catalyst system according to claim 2 wherein the transition metal is selected from groups 8–10 of the periodic table.

4. A catalyst system according to claim 3 wherein the transition metal is rhodium or platinum.

5. A catalyst system according to claim 4 wherein the transition metal is rhodium.

6. A catalyst system according to claim 1 where in the compound of component (b), R is hydrogen; $R_1$, $R_4$, $R_5$ and $R_8$ are tert-butyl; and $R_2$, $R_3$, $R_6$ and $R_7$ are hydrogen, methyl or tert-butyl.

7. A catalyst system according to claim 1 where in the compound of component (b), E and E' are each a direct bond, methylene or ethylidene.

* * * * *